United States Patent [19]
Theodore et al.

[11] Patent Number: 6,071,919
[45] Date of Patent: *Jun. 6, 2000

[54] ZWITTERIONIC COMPOSITIONS AND METHODS AS BIOLOGICAL RESPONSE MODIFIERS

[75] Inventors: T. Ronald Theodore, 3 Robinwood Cir. P.O. Box 513, Forestdale, Mass. 02644; Roscoe L. Van Zandt, Arlington, Tex.

[73] Assignee: T. Ronald Theodore, Forestdale, Mass.

[ * ] Notice: This patent is subject to a terminal disclaimer.

[21] Appl. No.: 08/983,269

[22] PCT Filed: Feb. 13, 1997

(Under 37 CFR 1.47)

[86] PCT No.: PCT/US97/02270

§ 371 Date: Nov. 2, 1998

§ 102(e) Date: Nov. 2, 1998

[87] PCT Pub. No.: WO97/29745

PCT Pub. Date: Aug. 21, 1997

Related U.S. Application Data

[63] Continuation-in-part of application No. 08/600,901, Feb. 13, 1996, Pat. No. 5,716,959.

[51] Int. Cl.$^7$ ................................................. A61K 31/395
[52] U.S. Cl. .............................. 514/255; 514/76; 514/77; 514/564; 424/531
[58] Field of Search ............................... 514/255, 76, 77, 514/564; 424/531

[56] References Cited

U.S. PATENT DOCUMENTS 4,753,942  6/1988  O'Sullivan ............................. 514/255

OTHER PUBLICATIONS

Stapleton et al., J Pharm Pharmacol 46:745–750, 1994.

*Primary Examiner*—Rebecca Cook
*Attorney, Agent, or Firm*—Richard P. Crowley

[57] ABSTRACT

A method of treating a disease in a mammal by administering a therapeutic effective amount of an amphoteric zwitterion compound as an active ingredient. A pharmaceutical composition which comprises an amphoteric zwitterionic compound as an active ingredient in combination with a carrier and other adjunctive pharmaceutical agents.

23 Claims, No Drawings

ZWITTERIONIC COMPOSITIONS AND METHODS AS BIOLOGICAL RESPONSE MODIFIERS

REFERENCE TO PRIOR APPLICATION

This is a 371 of PCT/US97/02,270 filed Feb. 13, 1997 which is a continuation-in-part application of U.S. Ser. No. 08/600,901, filed Feb. 13, 1996, now U.S. Pat. No. 5,716,959, issued Feb. 10, 1998, hereby incorporated by reference.

BACKGROUND OF THE INVENTION

In the world population, the incidence of cancer is very significant. It is estimated that one in four persons will develop cancer sometime in their life. Half of all persons who develop cancer will die from it. The incidence of cancer-related deaths has been doubling every thirty years in the United States. There are many factors associated with the increasing incidence of disease. Many people live longer, and the incidence may increase due to an aging population. Environmental toxins and/or genetic changes may also play a role in the increase.

There has also been an increase in the incidence of infectious diseases, particularly viral infections. Many virulent strains are now seen. Virally-mediated infections, such as hepatitis (A, B and C) and HIV-type infections have had a significant impact on the population. Some cancers, such as Kaposi's sarcoma, are associated with viral infections.

There are many diseases associated with autoimmune disorders. Rheumatoid arthritis and myasthenia gravis are examples. The etiology of many autoimmune diseases is not clear. Genetic and/or environmental aspects may contribute in several ways to alter hemopoietic and immune responses. Certain drugs may trigger autoimmune responses as well as induce immunosuppressed states.

There are four basic approaches to the treatment of cancer. These approaches are sometimes combined in the form of multimodality therapies. The basic approaches are surgical resection, chemotherapy, radiation and immunotherapy. Alternative approaches include naturopathy, herbal treatments and acupuncture.

Therapies for autoimmune disease have been limited. Primarily, the use of steroids has been a mainstay. Advanced cases of diseases, such as rheumatoid arthritis and myasthenia gravis, rarely respond well.

Infectious disease therapies have had many advances with the use of antibiotics. There have been a few antiviral compounds developed. Their use is fairly limited to a few types of infection. HIV is yet to respond to any significant therapy. Immune therapies have had limited success in hepatitis.

Over the last fifty years, there has been a slow development of various immunotherapies. These have included the use of specific cytokines, chemokines, lymphokines and other immunological substances derived from cell culture research and cloned. In the past, it has been shown that certain fractions of cell cultures have produced specialized responses in tumors. Chemotherapeutic agents and radiation have generated some tumor responses, but have high toxicity.

The need for developing agents and compositions that effectively treat cancer, cancer pain, immunologically-mediated diseases and certain infectious diseases continues to be very important.

SUMMARY OF THE INVENTION

The present invention relates to a method for the treatment of diseases in mammals by the administration of zwitterionic compositions as safe and effective biological response modifiers to the mammals and to the zwitterionic compositions used and the preparation of such zwitterionic compositions for use in treatment.

In particular, the invention concerns a method of treating mammals to stimulate the immunological system and to induce the production of hypercellular bone marrow and extramedullary hematopoiesis in the treated mammal.

The present invention demonstrates that zwitterionic molecules have a definitive effect as a biological response modifier (BRM). Zwitterionic molecules are substances that have neither a negative nor a positive charge. Zwitterions are compounds having a net charge on the molecule which is zero and which have positive and negative groups that are equally ionized in the molecule, and are dipolar molecules containing, for example, hydroxy groups and amino groups and also acid groups, like phosphoric, carboxylic or sulfonic acid groups, and, for example, generally having $pK_a$ in the range of 6.15 to 8.4.

A number of zwitterion compounds may be employed in the treatment of mammal diseases as active ingredients, either alone or in various combinations, and typically in combination with one or more solid or liquid pharmaceutically acceptable carrier materials. Many of such zwitterion compounds are recognized and used as buffers and not used or recognized as active ingredients in the treatment of diseases, such as the HEPES, PIPES, etc. compounds and the salts thereof.

Some zwitterion compounds useful in the invention are set forth in the following table:

| No. | Structure | Proposed Name | pK. at 20° | $\alpha pK_a$/° C. | Saturated Solution at 0° (M) | Metal-Buffer Binding Constants Log $K_M$ | | | |
|---|---|---|---|---|---|---|---|---|---|
| | | | | | | $Mg^{2+}$ | $Ca^{2+}$ | $Mn^{2+}$ | $Cu^{2+}$ |
| I | 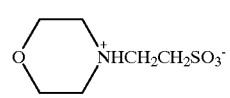 | MES | 6.15 | −0.011 | 0.65 | 0.8 | 0.7 | 0.7 | Negl |
| II | 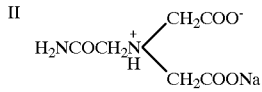 | ADA | 6.6 | −0.011 | — | 2.5[a] | 4.0[a] | 4.9[a] | 9.7[a] |

| No. | Structure | Proposed Name | pK. at 20° | $\alpha pK_a/°$ C. | Saturated Solution at 0° (M) | Metal-Buffer Binding Constants Log $K_M$ | | | |
|---|---|---|---|---|---|---|---|---|---|
| | | | | | | $Mg^{2+}$ | $Ca^{2+}$ | $Mn^{2+}$ | $Cu^{2+}$ |
| III | $NaO_3SCH_2CH_2\overset{+}{N}$⌬$\overset{+}{N}HCH_2CH_2SO_3^-$ | PIPES | 6.8 | −0.0085 | — | Negl | Negl | Negl | Negl |
| IV | $H_2NCOCH_2\overset{+}{N}H_2CH_2CH_2SO_3^-$ | ACES | 6.9 | −0.020 | 0.22 | 0.4 | 0.4 | Negl | 4.6 |
| V | $(CH_3)_3\overset{+}{\equiv}N\text{—}CH_2CH_2NH_2Cl^-$ | Cholamine chloride | 7.1 | −0.027 | $4.2^b$ | Negl | Negl | Negl | Negl |
| VI | $(HOCH_2CH_2)\overset{+}{=\!=}NHCH_2CH_2SO_3^-$ | BES | 7.15 | −0.016 | 3.2 | Negl | Negl | Negl | 3.5 |
| VII | $(HOCH_2)_2\overset{+}{\equiv}NHCH_2CH_2SO_3^-$ | TES | 7.5 | −0.020 | 2.6 | Negl | Negl | Negl | 3.2 |
| VIII | $HOCH_2CH_2\overset{+}{\underset{H}{N}}$⌬$NCH_2CH_2SO_3^-$ | HEPES | 7.55 | −0.014 | 2.25 | Negl | Negl | Negl | Negl |
| IX | $H_2NCOCH_2\overset{+}{N}H_2CH_2COO^-$ | Acetamido-glycine | 7.7? | — | Very large | — | — | — | — |
| X | $(HOCH_2)_3\overset{+}{\equiv}CNH_2CH_3COO^-$ | Tricine | 8.15 | −0.021 | 0.8 | 1.2 | 2.4 | 2.7 | 7.3 |
| XI | $H_2NCOCH_3NH_2$ | Glycinamide | 8.2 | −0.029 | $4.6^b$ | — | — | — | — |
| XII | $(HOCH_2)_3\equiv CNH_3$ | Tris | 8.3 | −0.031 | 2.4 | Negl | Negl | Negl | — |
| XIII | $(HOCH_2CH_2)_2\overset{+}{=\!=}NHCH_2COO^-$ | Bicine | 8.35 | −0.018 | 1.1 | 1.5 | 2.8 | 3.1 | 8.1 |
| XIV | $H_2\overset{+}{N}CH_2CONHCH_2COO^-$ | Glycylglycine | 8.4 | −0.028 | 1.1 | 0.8 | 0.8 | 1.7 | 5.8 |

[a]Data of Schwarzenbach et al. (1955).
[b]As the hydrochloride.

The zwitterion compounds of the table are characterized by one or two nitrogen-carbon bonds, either as aliphatic heterocyclic compounds or aliphatic compounds usually with an acid group ($COO^-$ or $SO_3^-$) and an alkaline group (OH, $N^+$, NH and $NH_2$).

One preferred zwitterion compound group as PIPES and HEPES comprises six membered heterocyclic rings with two nitrogen at each end and connected with divalent alkylidenes, like —$CH_2$— divalent radical, while MES is a heterocyclic compound with both oxygen and nitrogen in the ring with the NH group connected by $(CH_2)_{n\ 1-3}$ to an acid group. Thus, one group of zwitterion compounds useful, like HEPES, MES and PIPES, as an example, would have the structural formula:

$$\overset{H}{R_1\text{—}N^+\text{—}R_2\text{—}}\ \text{acid group,}$$

where $R_1$ and $R_2$ represent a $(CH_2)_{n\ 1-3}$, or $R_1$ is a nitrogen or oxygen as a part of a 5–6 member heterocyclic ring with $N^+$ or $N^+H$ as part of the ring, or where $R_1$ includes a nitrogen connected directly to $(CH_2)_{n\ 1-3}$, which alkylidene is connected to an alkaline group, like $NH_2$ or OH group.

The zwitterion compounds may include nitrogen and carbon groups, with $CH_2OH$ or $CH_2CH_2OH$ or $NH_2$ forming an alkaline end of the compound and $CH_2SO_3$ or $CH_2CH_2SO_3$ forming the other acid end of the compound.

The zwitterion compounds and their respective pharmaceutically acceptable salts which are preferred include HEPES, PIPES, MES, ADA and ACES, alone or in therapeutic combinations.

The amphoteric zwitterion compounds may be employed as active ingredients with other active ingredients, as well as other components and carriers typically used in pharmaceutical compositions; such as, but not limited to: buffers, stabilizers, dyes, antioxidants, dispersing agents, fillers, surfactants, silicones, bulking agents, pigments, salts, human or animal (natural or synthetic) cells and cellular components, antibiotics, drugs, vitamins, amino acids, proteins, serum and various other compounds and combinations thereof in varying amounts. The use of zwitterion compounds in pharmaceutical compositions used in treatment as an active ingredient have been shown; e.g. HEPES and PIPES, to provide macrophage infiltration of cancer tumors in dogs, and thus to provide an antitumor effect in the treatment of various diseases, and further demonstrate immune stimulating capabilities as evidenced in tests by the production of giant platelets and histiocytes.

It has been discovered that in tests in animals no evidence of toxicity is shown in doses up to 500 mg/kg. Some animals have received this dose three times in a twenty-four hour period. The dose schedule of zwitterion compounds as biologic response modifiers may vary depending on the disease and condition, but for treatment may range from about 0.1 mg/kg to 5000 mg/kg.

The immune stimulating effects of the zwitterion compounds have been demonstrated in animals. The tests show that at specific dose levels, all animals demonstrate the presence of giant platelets and histiocytes on peripheral smear.

The following results were found with HEPES in all test animals: 1) all treated dogs had rapid resolution of hematomas at the injection sites; 2) no animals in the treated group had any respiratory infections while being treated, many in the untreated group did; 3) all dogs became calm following injections; and 4) there was strong evidence of improved vascular integrity in the treated groups. There is evidence of marked diuresis at certain dosages suggesting an effect on renal function and/or antidiuretic hormone (ADH).

One amphoteric zwitterion compound useful in the invention, alone or with other compounds, zwitterion compounds or as other active ingredients or cell cultures in a therapeutic amount, comprises inhibited piperazine zwitterionic compounds, such as, but not limited to, an N-2 hydroxyl or amino alkyl piperazine-N-2 alkane acid, like carboxylic acid, phosphoric or sulfonic acid and its effective, non-toxic salts and derivatives and substituents. In particular, the invention is directed to the use of, and is particularly effective with, a zwitterion known as HEPES and its acid salts; e.g. sodium or potassium, known as N-2 Hydroxyethylpiperazine-N'-2 Ethane Sulfonic Acid, formula weight 238 (i.e. $C_2H_{18}N_2O_4S$) (HEPES). They have routinely been used in cell cultures as a buffer and, to date, were not suspected to have any effects on cells, physiologic pathways or disease processes.

It is now shown that HEPES and other zwitterionic compounds are true biological response modifiers (BRM). They effect positive changes in cancer, cancer pain, autoimmune disease and viral infections and toxic syndromes. They can be used alone and/or in combination with mammalian serum and/or in combination with cell culture supernatants utilizing mammalian serum. There appears to be a possible interaction with serum and/or cell culture supernatants. The bioactive pathways may be affected by various compositions of zwitterionic molecules. It remains clear that they can play a role as a biological response modifier alone or in combinations. These molecules induce antitumor activity, cause tumor volume and size reduction, induce tumor necrosis and/or lysis, reduce pain due to cancer, induce reduction of autoimmune activity in autoimmune-mediated disease, reduce inflammatory processes and possess antiviral activity.

The mechanisms of action may be singular or multiple involving physiological, pathophysiological and immunological pathways. There may be effects of activating and/or stimulating and/or blocking specialized pathways and/or specialized receptor sites. There is a positive effect on the hemopoietic system. There appears to be effects on cell product secretion of many forms. These effects are beyond that of buffering capacity as evidenced by the effect on disease processes.

There may be further effects at the ionic level as well as distinct effects on membrane stability and permeability. Membrane stabilization may play an important role in causing abnormal cell division and abnormal cell function to normalize, either by external physiogenic factors or internal cellular functions, or both. In any event, this first description of the unique abilities of HEPES as a zwitterionic molecule and the effect upon disease processes is submitted.

The present invention relates to methods and compositions for inducing antitumor activity, tumor volume reduction, reduction of pain in cancer patients, induction of anti-inflammatory response in autoimmune-mediated disease, reduction of the activity and progression of immunologically-mediated diseases, induction of the regression of tumor growth, induction of the regression of autoimmune activity in immunologically-mediated disease and antiviral effects. The invention shows a unique capability for inducing certain biochemical, physiological and immunological responses that cause lysis and/or necrosis of tumors and slowing the progression of diseases, including cancer, autoimmune disease and diseases caused by viral infection. In particular, the use of HEPES (N-2 Hydroxyethylpiperazine-N'-2 Ethane Sulfonic Acid), a zwitterionic molecule used generally as a buffer in salts or cell cultures, has demonstrated effects that are antitumorgenic, analgesic, anti-inflammatory, reduction and/or progression of autoimmune diseases, and antiviral activity when used in certain compositions, alone or in conjunction with cell cultures. Additionally, HEPES appears to have an effect on cell culture immunological characteristics that are unique and not directly related to its buffering capability.

The present invention provides an effective treatment that is relatively non-toxic and safe. Its individual uniqueness is shown in many ways. For years, HEPES, a zwitterionic molecule, has been used as a buffer in mammalian cell cultures. It was not believed to have any specialized effects on cells. Certainly, it has not been viewed as an independent agent to treat cancer, cancer pain, autoimmune disease or certain infectious states, or to induce extramedullary hematopoiesis. It is now shown that HEPES ($C_5H_{18}N_2O_4S$) (N-2 Hydroxyethylpiperazine-N'-2 Ethane Sulfonic Acid) and its homologs and analogs can, in certain preparations, have antitumorgenic effects on tumor growth, volume reduction, tumor activity and cancer pain. It also has an effect on reducing or reversing certain autoimmune diseases. Additionally, it appears to have antiviral effects. HEPES has been used as a buffer in cell culture technology. The invention became apparent when use of HEPES and human serum without cell culture was given as a control to patients who were intended to receive certain cell culture supernatants for experimental treatment of cancer, cancer pain and immune disease and viral infections.

All of the above effects can be shown when the HEPES is used alone or in combination with other biological compositions where the effect may be potentiated through specialized physiologic, biochemical and immunologic actions. It may potentiate production of known and unknown substances in mammalian cell cultures, the combinations of which may render more active compositions notwithstanding the individual effects of the substance. It further is noted that the effects described are clearly demonstrated outside of cell culture technology. Thus, for example, HEPES is an immunological activator by itself. This would categorize HEPES as a true biological response modifier (BRM).

The present invention provides a method of preparing zwitterionic compositions for administration to a subject and the use of same compositions for the treatment of cancer, cancer pain, autoimmune diseases and infectious diseases.

The compositions used for administration comprise:
  a) preparing certain concentrations of HEPES in solutions alone and/or with amino acids and/or L-glutamine and/or with bicarbonate;
  b) preparing certain concentrations of HEPES in solutions with amino acids and/or L-glutamine and/or bicarbonate and/or human serum; and c) preparing certain concentrations of HEPES in solutions with amino acids and/or L-glutamine and/or bicarbonate and/or human serum and combining same with mammalian cell cultures, whether same cells in culture are transformed or not transformed, and using the supernatant and/or fractions of the supernatant alone or in combination to potentiate cellular production of immunological substances that are effective in working as biological response modifiers alone or in combination with zwitterionic compounds.

Also provided is a single or composition biological response modifier produced by the above methods.

The invention also provides a method of activating the immune system of a subject, comprising the above compositions when administered in an amount of the claimed compositions such that the immune system is activated. "Activating" can include activating, for example, a stimulator or blocker of immune activity.

Further provided is a method of increasing $CD_2$, $CD_3$, $CD_8$, and $CD_{20}$ counts and increases in stem cell production in subjects who are healthy or immunosuppressed comprising administration of a zwitterionic molecule, like HEPES, in compositions as described that effect increases in certain hemopoietic mechanisms.

It has been further discovered that the use of zwitterionic compounds particularly, but not limited to, HEPEs and its pharamacuetical salts in in vivo tests of both dogs and humans partuculary by intravenous and oral application, induce hypercellular bone marrow and induce extramedullary hematopoiesis in patients. Further, the zwitterionic compounds reduce the mean inhibitory concentration (MIC) of susceptible antibodies in culture (in vitro) and enhances antibiotic activity in vivo. The zwitterionic compound may be used alone or with a carrier, such as sterile water or a saline solution. Enhancement and inducement of extramedullary hematopoiesis has been found in amounts of HEPES administered in an amount of about 18–20 mg/kilograms or greater for e.g. 40 mg/kg of body weight in dogs with daily intravenous injections over a defined time period of 1–2 weeks.

Also provided is a method of reducing tumor size and/or volume comprising administrating to the subject a composition containing HEPES, a zwitterionic molecule, in a tumor-reducing amount, compositions such that tumor size and/or tumor volume is reduced. Further, that the induction of tumor lysis and/or necrosis occurs due to the biological response modifier effect of HEPES as a zwitterionic compound.

The present invention provides a method of treating autoimmune diseases in a subject, comprising administering to the subject an amount of the compositions containing HEPES, a zwitterionic molecule, such that the progression of the autoimmune disease is slowed and/or reversed, the effect of which is due to HEPES as a biological response modifier.

Also provided are methods of treating pain due to inflammation and/or tumor activity and/or autoimmune disease activity comprised of administering an amount and certain compositions containing a zwitterionic molecule, like HEPES or PIPES, to the subject.

Additionally provided are methods of treating viral infections in a subject comprising of administering an amount of the zwitterion compositions as the active ingredient resulting in a decrease of viral activity.

Also provided are methods of treating immunosuppressed and/or immunodepressed subjects whose pathophysiological state may have been induced by drugs, toxins, radiation or environmental factors, by administering an amount of HEPES alone or by compositions.

The present invention provides methods of preparing solutions containing amphoteric zwitterion compounds, like HEPES, as: a) the active ingredient in solutions with HEPES and/or amino acids and/or L-glutamine and/or bicarbonate; b) the active and/or activating agent in solutions containing HEPES and/or amino acids and/or L-glutamine and/or bicarbonate and/or mammalian (human) serum; and c) HEPES and/or amino acids and/or L-glutamine and/or bicarbonate and/or human serum and/or human (mammalian) serum in cell culture. Cells used in cell culture preparations were human B lymphoid cells from a healthy donor. The cells had been transformed or activated by prior exposure to Epstein-Barr virus (EBV) which is confirmed by the presence of Epstein-Barr virus nucleic antigen (EBNA). Approximately sixty percent (60%) of the human population is Epstein-Barr virus nucleic antigen positive. There are other methods for cell activation, such as endotoxin stimulation and protein activation stimulation (PAS) techniques, which are known to those of skill in the art. Further, the cells used are IgM secreting, and this is not considered a limiting factor. The preparations containing HEPES in cell culture may be further combined by the presence of HEPES in terms of immunologically activating and/or stimulating and/or blocking effects of other cell secreted substances. The effects on cancer, cancer pain, autoimmune diseases and viral infections may be increased further by HEPES. It may be that the action of HEPES as a biological response modifier may be enhanced by the presence of certain substances secreted by cells in culture and/or HEPES or the substances may have synergism in activity and/or certain immunological pathways are activated, stimulated or blocked when HEPES is added to cell cultures due to one or more immunophysiological pathway actions. It is further acknowledged that additional and/or the same mechanisms are present when HEPES is combined with human serum. The serum may contain certain immunologically active substances that when combined with HEPES are potentiated and/or certain substances when combined with HEPES cause activation and/or stimulation and/or blocking of specialized pathways.

Additionally, HEPES, a biological response modifier, used alone or in various compositions, or other zwitterionic molecules, has shown effectiveness by positive indicators, such as, for example, tumor lysis and/or necrosis; decrease in the number and/or distribution of lesions; decrease in tumor size and/or volume; decrease in tumor markers; decrease in pain and/or analgesic usage; increase in immunological and hemopoietic markers; decrease in inflammation and markers associated with inflammatory processes; decrease in total viral loads; and decreases in auto antibody production in immune-mediated disease.

The present invention provides a method for activating or enhancing the immune system by stimulating and/or blocking and/or other immunophysiologic pathway effects consistent with a BRM, comprising administering to a subject an amount of a zwitterion compound, like HEPES or PIPES, in the compositions set forth. Indicators consist of increases in stem cell production, $CD_2$, $CD_3$, $CD_8$ and/or $CD_{20}$ counts. Other markers may include decreased antibody titers, rheumatoid factor (RF), antinuclear antibody (ANA) and anti-acetylcholine antibody. Positive changes in certain immunological cell secreted substances include, but are not limited to, cytokines, chemokines, kinases, immunoglobulins and other known biological response modifiers. Improvement is noted in subjects with rheumatoid arthritis and myasthenia gravis. Hemopoietic indicators show positive responses for immunosuppressed and immunodepressed states due to drugs, chemotherapy, radiation, toxins and/or environmental effects. Further positive hemopoietic indicators related to virally induced, immunosuppressed states in addition to cluster determinants and stem cells include P-24 antigen and beta-microglobulin levels. This invention contemplates all of the above embodiments and continues.

It has been found that HEPES, or other zwitterionic molecules and/or compositions, produces giant platelets and histiocytes in blood demonstrating immune stimulating capability of zwitterionic molecules, and further, shows bone marrow stimulation. Zwitterion compounds, like HEPES, administered to mammals produces macrocytic invasion of tumors demonstrating antitumor activity.

The invention further demonstrates that a zwitterionic molecule is shown to be a biological response modifier when HEPES, or other zwitterionic compositions, is used alone or in combination, and administered to the subject, and results in tumor size and/or volume reduction and tumor lysis and/or necrosis. Tumor size, volume and necrosis can be detected and monitored by methods utilizing computerized axial tomography (CAT) and/or nuclear magnetic resonance imaging (MRI) and/or nuclear medicine scans, as known to those of skill in the art. Any tumor that is reduced or necrosed by this method utilizing HEPES or other zwitterionic molecules in the described compositions can be treated by this method, for example, tumors of ectodermal, mesodermal and endodermal age origin, such as tumors associated with non-Hodgkins lymphoma; adenocarcinomas, mesothelioma, squamous cell carcinoma; embryonic testicular carcinoma; breast carcinoma; prostate carcinoma; ovarian carcinoma; gall bladder carcinoma, including signet cell type; cholangitic carcinoma; esophageal carcinoma; malignant melanoma; lung carcinoma; hepatoma; multiple myeloma; Kaposi's sarcoma; seminoma; brain tumor, including astrocytoma and glioblastoma, hepatoma, among many others, and further, that the tumor may be primary or metastatic as exemplified by the examples.

It has been discovered that zwitterion compounds provide a method of inducing a diuretic effect in mammals. The diuretic effect includes the ability of zwitterionic molecules to effect renal function and effect antidiuretic hormone (ADH) activity. The ADH method improves respiratory function and/or increases oxygen efficiency and/or improves oxygen-carbon dioxide exchange in lung tissue and includes favorable responses in emphysema, cystic fibrosis and asthma.

Also provided by the invention is a method of treating autoimmune diseases in a subject, comprising administering to the subject an amount of HEPES alone or other zwitterionic molecules in the described compositions such that the progression of the autoimmune pathology and/or pathophysiology of the disease is slowed, stopped or reversed. For example, the method can halt wasting, lower antibody titers, increase appetite, improve sleep and increase energy. The preferred method of composition utilizing HEPES alone or other zwitterionic molecules, alone or in compositions as previously described. Any autoimmune disease that responds favorably to this method, as can be tested, as taught herein, can be treated by this method, such as acquired immunodeficiency syndrome (AIDS); rheumatoid arthritis; myasthenia gravis; psoriasis; glomerulonephritis; thyroiditis; systemic lupus erythromatosis; multiple sclerosis; amyotrophic lateral sclerosis (AML); diabetes; aphthous stomatitis; lichen planus and chronic fatigue syndrome.

The present invention also provides a method of reducing a lesion caused by a virus in a subject, comprising administering an amount of HEPES alone or other zwitterionic molecules in the described compositions, such that the lesion is reduced. Preferred methods of composition are as previously described. Lesion progression and involvement can be monitored by standard methods known to those of skill in the art, for example, blood tests, antibody titers, measurement of lesions, as well as other evaluation techniques known to those of ordinary skill in the art. Lesions produced or induced by any virus that are reduced by this method are included in this invention; as can be tested by the methods herein, for example, Kaposi's sarcoma; herpes simplex; herpes zoster; and genital herpes.

The invention further provides a method of reducing the intensity and duration of a viral infection in a subject comprising administering to the subject an amount of HEPES or other zwitterionic molecules in the described compositions, such that the intensity and duration of the viral infection are reduced. The preferred method of treatment utilizes the methods of compositions previously described. The method can be utilized for any viral infection, the intensity and duration of which is reduced by the administration of a composition of the present invention, by the claimed method, as can be tested by the methods herein. Such viral infections are exemplified by the examples and can include, for example, infection by influenza viruses; rotavirus; adeno viruses; herpes viruses; immunodeficiency viruses and coxsackie viruses.

The use of zwitterion compounds provides a method of effecting changes directly and/or indirectly on serotonin and acetylcholine production and activity. The method includes a membrane stabilization effect resulting in antiarrythmagenic effects, antiseizure effects and improved cell survival in trauma or physiologic injury. It results in reduced tissue damage in myocardial infarction and cerebral vascular accidents. Other such effects include reduced nerve cell injury and/or nerve cell repair and/or nerve cell regeneration.

Further provided by this invention is a method of reducing pain and/or inflammation in a subject, comprising administering to the subject an amount of HEPES alone or other zwitterionic molecules in the described compositions, such that pain and/or inflammation are thereby reduced. A preferred method of treatment utilizes the methods of compositions as previously described. Pain remission can include remission of pain from a decrease in tumor size and/or volume, or in space-occupying lesions, thus decreasing organ pressure and compression of anatomical structures (i.e. nerves, vessels and other organs), as well as remission of pain not associated with a decrease in tumor size or volume or capsular stretching or a decrease in lesions, such as pain in bones and other pain that occurs before a significant decrease in tumor size or volume or lesion occurs. Such pain reduction may also be due to remission or reduction of inflammatory processes as in rheumatoid arthritis or other inflammatory and/or autoimmune diseases. Pain remission may also be due to changes in other physiologic, pathophysiologic and immune pathophysiologic improvement, such as: changes in production of endorphins and similar biochemicals; changes in nervous system activity and changes in ionic conditions and/or membrane permeability and/or membrane stability of a cellular or physiologic pathway levels.

A method of reducing effects of mental depression in a subject is also provided comprising administering to the subject an amount of HEPES alone or other zwitterionic molecules in the described compositions, such that the effects of mental depression are reduced. A preferred method of treatment utilizes the methods of compositions as previously described. Effects that are within this invention are those that can be reduced by this method, as can be tested by the methods taught herein and by standard protocols for measuring such effects. Examples of effects which can be reduced by this method include insomnia, weight loss, sadness/melancholy, clinical depression and feelings of isolation. Some results from this method include increased appetite, sense of well being, reduced anxiety, calmness, mood elevation and improved quality of sleep.

Also provided is a method of treating cancer in a subject comprising administering an amount of HEPES alone or other zwitterionic molecules in the described compositions, such that the progression of cancer is slowed, stopped or reversed. A preferred method of treatment utilizes the methods of compositions as previously described. Cancers included in this method are those which are reduced by this method as can be tested given the teachings herein. Some examples of such cancers include breast cancer; prostate cancer; non-Hodgkins lymphoma; cholangitic cancer (including signet cell type); glioblastoma; and others as previously stated. The cancers may be primary or metastatic. They include all cancers of ectodermal, mesodermal and endodermal origin.

The invention comprises a method of improving visual color perception, increased visual acuity, improved depth perception, improved hearing and improved taste. Other cellular effects include promotion of hair growth. The method includes treating toxic syndromes, such as Gulf War Syndrome and/or Agent Orange toxicity and/or other such syndromes that are related to organic phosphate induced disease, disease strands and/or polyneuropathies.

Further provided herein is a method of treating hepatitis in a subject comprising administering to the subject an amount of HEPES alone or other zwitterionic molecules in the described compositions, such that the pathologic and pathophysiologic activity of hepatitis is reduced. Such pathologic and pathophysiologic activities that are reduced by this method include, for example, elevated bilirubin levels and hepato-spleno-megaly. A preferred method of the treatment utilizes the methods of composition previously described. By "hepatitis", it is meant to include, for example, hepatitis A, hepatitis B, hepatitis C (formerly non-A, non-B) and alcoholic hepatitis.

Also provided herein is a method of reducing side effects of chemotherapy and radiation therapy in a subject comprising administering to the subject an amount of HEPES alone or other zwitterionic molecules in the described compositions, such that the side effects of chemotherapy and radiation therapy are reduced. A preferred method of treatment utilizes the compositions previously described. Side effects which can be reduced included nausea, vomiting and hair loss.

The administration of the amphoteric zwitterionic compound also has been demonstrated to produce antispasmodic effects (affects muscle, smooth and striated) activity and promotes hair growth in animals.

The invention also comprises a method of treating blood coagulation disorders in effecting changes in fibrin and fibrinogen activity. Such pathologic activities include, for example, hypercoagulable states and/or hypocoagulable as may be seen in genetic disorders and/or certain pathophysiologic states, including sepsis and/or drug induced coagulation disorders and/or other metabolic disturbances.

The present invention also provides a method of detecting infection in a subject comprising administering HEPES alone or other zwitterionic molecules in the described compositions to the subject and monitoring development at a reaction, such as fever, chills, diaphoresis and/or rigor by the subject, such development indicating presence of infection in the subject. A rapid search for infection can be accomplished whether such infection is clinical or sub-clinical with the etiology being bacterial, fungal or viral. It is further contemplated that the reactions of fever, chills and rigor may be immunologically mediated and therefore in vitro testing for immunological substances using controls against the subjects blood and/or cells would be developed. This may include measurement of cytokines (possibly IL-1 or others), chemokines, kinases and other cell-secreted products.

Further provided herein is a method for treating Alzheimer's disease, senile dementia and Creutzfeldt-Jakob disease, in a subject comprising administering to the subject an amount of HEPES alone or other zwitterionic molecules in the described compositions, such that the pathologic and/or pathophysiologic activities are slowed and/or reversed. Such pathologic or pathophysiologic activities that are slowed or reversed by this method include, for example, improved memory, improved coordination, decreased agitation and improved quality of life. A preferred method of the treatment utilizes methods of composition previously described.

The compositions may be administered parenterally; e.g. sublingually, intrathecally, intravenously, intramuscularly; subcutaneously, and the like. Oral preparations and topical preparations (HEPES in glycol gels and in amounts like sun tan lotion) are shown to be effective. The exact amount of a composition required will vary from subject to subject, depending upon species, age, weight, general condition of the subject, the severity of the disease that is being treated, the mode of administration used and the like. Thus, it is not possible to state an exact amount. Generally, dosages of 1000 mg, or more, in compositions described may be given intravenously daily. Dosages of 35 grams intravenously daily have been given with responses noted in some diseases. There have been complaints of headache and fatigue in a few subjects at higher dosages (<10%). Toxicity studies have shown no toxic effects at 500 mg/kg response levels for each disease. Dosage may vary from less than 0.01 mg/kg to greater than 1 gram/kg daily intravenously, orally, sublingually, intrathecally or topically. Length of therapy is yet to be determined.

Depending upon the intended mode of administration, the compositions can be in pharmaceutical compositions in solid (tablets, capsules), semi-solid (topical gels, ointments) or liquid (injection, oral) forms. The total effect of a biological response modifier depends upon many variables, including compositions which as described may have increased effects depending upon type of disease and pharmaceutical form. As described, compositions may have HEPES alone or other zwitterionic molecules alone or with mammalian serum or with supernatants or supernatant fractions, filtered or unfiltered, each having different bioactivity and biological response modifier capability on different disorders and diseases. In addition, depending upon mode of administration and the composition, the composition may be provided with pharmaceutically acceptable carriers and, in addition, may include any other medicinal agents, pharmaceutical agents, carriers, adjuvants, diluents, etc., that do not interfere with the activity of the composition, for example, saline solutions.

The present invention is more particularly described in the following examples which are intended as illustrative only, since numerous modifications and variations therein will be apparent to those skilled in the art.

The zwitterionic molecular compounds useful in treatment many vary in effective, therapeutic concentrations depending upon the disease and condition of the mammal. However, generally effective, therapeutic concentrations range from about a low of 0.001 mg/kg to as high as 5000 mg/kg, such as to 500 mg/kg, or more. Various dose response ranges are, for example, but not limited to: for reduction in pain of 1 mg/kg to 20 mg/kg; and for generation of platlets, antieffect and immune stimulatory effects of over 10 mg/kg, such as 20 mg/kg to 100 mg/kg or more. The administration may vary and range from daily or more dosages over selected time periods of 1–12 weeks or more depending on the patient's condition and the disease to be treated. The zwitterion compounds are used alone or in combination with other representative pharmaceutical carrier compounds, like saline solution bulking agents, stabilizers, inert ingredients, or other active ingredients, such as amino acid compounds, like, but not limited to, carbohydrate amines, like L-glutamine, in varying amounts, for example, of 0.01 mg/kg to 1 gram/kg. Other amino acids for use with HEPES include L-alanine; L-Araline HCl; L-Asparagine-$H_2O$; L-Aspartic Acid; L-Cystine-2HCl; L-Glutamic Acid; Glycine; L-Hstidine-HCl-$H_2O$; L-Isoleucine; L-Leucine; L-Lysine-HCl; L-Methionine; L-Phenylalanine; L-Proline; L-Serine; L-Tryptophan; L-Tyrosine-2Na; L-Valine; as well as vitamins including d-Biotin; D-Ca Pantothenate; Choline Chloride; Folic Acid; i-Inositol; Nicotinamide; Pyridoxine-HCl; Riboflavin; Thiamine-HCl and Vitamin $B_{12}$. Typically, the zwitterion molecular compositions are employed in sterile liquid form in saline solutions, such as in syringes or intravenous containers or bags, and contain a buffer agent, such as phosphate or bicarbonate or other buffers, like sodium and potassium, in saline solution.

Piperazine zwitterion compounds of the invention include zwitterion piperazine compounds with an hydroxyl and a sulfonic acid group and the pharmaceutically acceptable salts like those compounds having the structural formula:

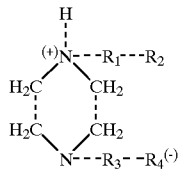

wherein $R_1$ is an N-linking group, like a divalent hydrocarbon, e.g. alkyl group, such as $C_1$–$C_6$; $R_2$ is an alkaline group like a hydroxyl or amine; $R_3$ is an N-linking group, like a divalent hydrocarbon e.g. alkyl, such as $C_1$–$C_6$; and $R_4$ is an acid group or substituted acid, like citrate, adipic, carboxylic (COOH); phosphoric ($PO_4OH$) or sulfonic ($SO_2OH$) acid and the salts of the zwitterion compound.

The zwitterion molecular compositions also useful contain human serum in effective and carrier amounts, like A, O, B and particularly, AB human serum certified to be negative for bacteria, mycoplasma, hepatitis, TB, HTLVI AND II, and other infectious agents or components.

Some representative compositions prepared and useful in the invention are:

Compositions of Zwitterionic Molecular Compounds

Type A
 100–300 mg HEPES ultra pure
 1.6 cc L-glutamine
 Amino acids
 Bicarbonate buffer Type B
 100–300 HEPES ultra pure
 1.6 cc L-glutamine
 0.8 cc human AB serum
 Amino acids
 Bicarbonate buffer Type C
 100–300 mg HEPES
 1.6 cc L-glutamine
 0.8 cc–1.0 cc human AB serum Normal administration was in 50 cc normal saline (0.9% saline solution) given intravenously over 15–30 minutes.

DESCRIPTION OF THE EMBODIMENTS

The present invention may be understood more readily by reference to the following detailed description of specific embodiments and the examples included therein.

EXAMPLES

Example One

A sixty-five year old white male with a five year history of prostate cancer. The patient had multiple metastases to bone sites. His pain was intense. He was receiving 400 mg of morphine, 6 Dilaudid tablets and 3 Darvocet-N tablets daily.

The patient was given a composition of 300 mg HEPES, 1 cc human serum, 1 ml L-glutamine with amino acids and bicarbonate combined with a human cell culture supernatant (intravenously with normal saline) daily for one month. At the end of the month, the patient had significant pain reduction. He required no narcotics at all and took occasional non-steroidal anti-inflammatory medication for occasional discomfort. His Prostatic Specific Antigen (PSA) had declined to 50% from baseline.

Example Two

A sixty-two year old Korean male with a two year history of pancreatic carcinoma with documented extension. The patient had severe pain with duct obstruction and was moribund. He was unable to eat or take fluids orally. He was receiving 35 mg of Demerol per hour intravenously.

The patient was given 100 mg HEPES, 0.8 cc human serum, 1.6 cc L-glutamine with amino acids in normal saline (50 cc) twice daily for two weeks (no cell culture). At the end of five days, his IV Demerol was reduced to 15 mg per hour. After seven days, he was receiving 5 mg per hour. He was able to take soft solids and fluids. He could stand unassisted. After two weeks, he required only oral Demerol and was comfortable and functional. His tumor marker CA 19-9 had decreased more than 25% from baseline.

Example Three

A sixty-five year old white male with signet cell carcinoma of the gall bladder with extensive retroperitoneal involvement. He was unable to eat. His carcinogenic embryonic antigen (CEA) level was 1300. His liver functions showed an alkaline phosphatase>450 mg/ml, SGOT>100, SGPT>60, LDH>200. He was taking morphine for pain.

The patient was given 300 mg HEPES, 0.8 cc human serum, 1.6 cc L-glutamine with amino acids (no culture supernatant) intravenously in 50 cc normal saline daily for four weeks. After four weeks, his CEA level fell to 600. His liver function SGOT, SGPT and LDH were normal. Alkaline phosphatase was<200. He was essentially pain free. He could take liquids and soft solids.

Example Four

A fifty-eight year old female with a greater than a five year history of severe rheumatoid arthritis. She had severe pain. She had failed to respond to gold and methotrexate therapy.

She was given 300 mg HEPES, 1.6 cc L-glutamine (no human serum, no cell culture) in 50 cc normal saline for two weeks. After two weeks, she had no significant pain. Non-steroidal anti-inflammatories (NSAIDs) was the only medication needed for her to be mobile and comfortable. Her erythrocyte sedimentation rate (ESR) was 50% of baseline. Rheumatoid factor and ANA were decreased.

Example Five

A seventy-two year old male with a ten year history of recurrent Kaposi's sarcoma. All previously removed. No evidence of internal malignancy. Patient had a recurrence on the right foot.

Patient was given 300 mg HEPES, 1.6 cc L-glutamine, 0.8 cc human serum with amino acids in 50 cc normal saline IV three times a week. He also received 30 mg HEPES, 0.1 cc human serum, 0.2 cc L-glutamine with amino acids as an intralesional injections three times a week (total 5 cc volume). After four weeks, the lesions disappeared and have not returned. Kaposi's sarcoma is a virally-mediated tumor.

It is discovered that zwitterionic compounds, such as HEPES, decrease the production of alkaline phosphatase in mammals. At concentrations of approximately 12 mg/kg the effect appears to start, while at concentrations in excess of 100 mg/kg to 500 mg/kg or greater, baseline levels of alkaline phosphatase fall by a factor of two or greater, and in some cases it is not measurable by standard laboratory methods.

Example Six

Five healthy canines were administered up to 500 mg/kg of HEPES. At these doses, serum alkaline phosphatase was not detected by standard laboratory methods in all canines.

To date, more than twenty-five patients have been treated with 300 mg/kg to 1000 mg/kg HEPES daily (no other agents or additional compositions). All patients with cancer pain have responded with pain reduction. All patients with cancer have had a decrease of twenty-five to fifty percent (25%–50%) in tumor volume and/or tumor activity. All patients with rheumatoid arthritis and myasthenia gravis have had a twenty-five to fifty percent (25%–50%) reduction in disease activity.

Example Seven

Five healthy beagle dogs (males and females) were given 18 mg/kg intravenously of zwitterionic piperazine compound (HEPES) for one week. The dose was increased to 40 mg/kg for one week. All dogs had a bone marrow biopsy and a liver biopsy after two weeks. In all cases, the bone marrow became hypercellular. This is also consistent with immune stimulating effect. In all cases, the liver evidenced the presence of megakaryocyte production consistent with induced extramedullary hematopoiesis. All animals had an increase in circulating histiocytes and giant platelets.

Example Eight

A male with organophosphate induced polyneuropathy (such as found in Agent Orange toxicity and/or Gulf War Syndrome) had significant numbness in both legs, decreased sensation in both hands, and decreased proprioception was given 8 mg/kg orally of zwitterionic piperazine (HEPES) for two weeks. At the end of two weeks, sensation and proprioception had returned. The medicine was stopped and symptoms returned in two weeks. The zwitterionic piperazine was reinstated and in two weeks sensation and proprioception were again restored. The zwitterionic HEPES preparations counteract the effect of the organic phosphate induced toxicity and disorders and reversed the effect of organic phosphate induced polyneuropathy in the patient and restored myelin integrity.

Example Nine

A female with painful Herpes Zoster unresponsive to conventional treatment was given 1000 mg intravenously of zwitterionic piperazine daily. On the second day, the pain had diminished, so that other analgesia was not required. On the third day, the lesions had crusted and were clearly healing. On the seventh day, there was no pain at all and the lesions had healed.

Example Ten

A male with documented HIV infection had HIV associated polyneuropathy. He could not raise his legs without assistance. He was given 5000 mg intravenously of zwitterionic piperazine (HEPES) daily for thirty days. After thirty days, he could raise his legs without assistance. His cluster determinates had risen and sensation and proprioception were improved. Total viral load ad determined by PCR is decreased, which demonstrated that the HEPES had an anti-viral capability and was effective against neurological sequelae of viral diseases.

Example Eleven

A female with a known history of chronic hepatitis B infection had a bilirubin level of 5.0 and elevated liver enzymes. She was given 5000 mg intravenously of zwitterionic piperazine (HEPES) for thirty days. After thirty days, her bilirubin fell to 3.0 and other liver enzymes were reduced by 25 percent or more.

Example Twelve

Routine agar gel cultures are inoculated with beta-hemolytic streptococci and gram negative staphylococci. The cultures were raised to colony counts of $10^6$. The mean inhibitory concentration (MIC) with susceptible antibiotics was measured with and without the presence of zwitterionic piperazine (HEPES). In each case, the presence of the zwitterion caused a decrease in MIC of each antibiotic in culture (in vitro) of more than 10 percent and enhanced the antibiotic efficacy in vivo.

Example Thirteen

Two females with urinary tract infections (*E. coli*) received Bactrim DS for three days. Both patients are still culture positive with symptoms at the end of seven days. Each patient is given Bactrim DS, one dose with 3000 mg zwitterionic piperazine orally for three days. After three days, both are culture negative and symptom free.

Example Fourteen

A 62 year old man with ventricular irritability, 4–6 premature ventricular contractions per minute (PVCs), was not controlled with Prancetyl, Quinidine, or beta blockade. He was taking no medicines and was started on 3000 mg zwitterionic piperazine orally for seven days. At the end of seven days, the patient had only occasional PVC (1 every 10 minutes).

Example Fifteen

A 26 year old female with a longstanding history of seizure disorder was poorly controlled and had recurrent seizures while taking Dilantin and phenobarbital. She started on 5000 mg zwitterionic piperazine orally (2500 mg twice a day) for two weeks. After two weeks of zwitterionic piperazine, the patient's EEG showed significantly decreased focal activity. The zwitterionic piperazine (HEPES) has membrane stabilizing properties, is effective for anti-arrhythmic therapy, and is effective anti-seizure therapy.

Example Sixteen

A 10 year old female presented with acute hymphocytic leukemia (ALL). She had been treated with conventional therapy and an experimental protocol. Despite these treatments, she has failed to respond and persisted in blast crisis.

She was started on zwitterionic piperazine therapy (HEPES). Initial dose was 13.0 mg/kg I.V. On day four she was progressively increased to 80 mg/kg I.V., and she was then maintained at 80 mg/kg I.V.

Her baseline laboratory data was obtained following a blood transfusion before starting the HEPES;

Day 1
  (pre-infusion Hemoglobin (Hgb)) 10.5 g/dl
  Platelets 31,000
  White Blood Cells (WBC) 38,000
  Blasts 45%
Day 3 of HEPES treatment
  Hgb 8.5 g/dl
  Platelets 14,000
  WBC 53,000
  Blasts 45%
Day 7 of HEPES treatment
  Hgb 11.6 g/dl
  Platelets 17,000
  WBC 6,300
  Blasts 5.0%

The data clearly shows a cessation of the blasts crisis. Platelet destruction has ceased. The example shows that HEPES is effective as a biological response modifier in the treatment of bone marrow cancers like leukemia and reduces significantly blast crisis in leukemia patients.

What is claimed is:

1. A method for treating a disease in a mammal, selected from the group consisting of: an infectious disease; a cancerous tumor; leukemia; and an autoimmune disease, which method comprises: administering to the mammal with the disease, as a biological response modifier, an effective amount in one or more treatments, of a zwitterion composition comprising an amphoteric zwitterion compound or a pharmaceutically acceptable salt thereof, which zwitterion compound is an aliphatic or heterocyclic compound having at least one carbon-nitrogen bond and having an acid group selected from the group consisting of: $SO_3$; $PO_3$; and COO; and an alkaline group selected from the group consisting of: OH; $N^+$; $N^+H$; and $NH_2$.

2. The method of claim 1 wherein the zwitterion compound has a six member heterocyclic ring with a nitrogen atom as a part of the ring.

3. The method of claim 1 which comprises administering from about 0.1 mg/kg to about 5000 mg/kg of the zwitterion compound per body weight of the mammal.

4. The method of claim 1 wherein the zwitterion composition comprises an amino acid and human serum.

5. The method of claim 1 wherein the treatment of the disease is enhancing the efficacy of an antibiotic administered to the mammal.

6. The method of claim 1 wherein the treating of disease is reducing blast crisis in leukemia treatments.

7. The method of claim 1 wherein the treating of the disease is the treating of the autoimmune disease hepatitis.

8. The method of claim 1 wherein the treating of the disease is reducing the level of alkaline phosphatase in a mammal.

9. The method of claim 1 wherein the zwitterion compound has a 5 or 6 membered heterocyclic ring with two nitrogen atoms or a nitrogen and an oxygen atom in the ring.

10. The method of claim 1 wherein the zwitterion compound has one or more —$CH_2OH$ groups and a —$CH_2$ COO acid group connected to an intermediate nitrogen atom.

11. The method of claim 1 wherein the zwitterion compound has a pH at 20° C. of 6.15 to 8.4.

12. The method of claim 1 which comprises administering orally over a selected time period from about 0.1 mg/kg to 500 mg/kg of the zwitterion compound per body weight of the patient.

13. The method of claim 1 wherein the zwitterion compound is selected from the group consisting of N-(2-hydroxyethyl)piperazine-N'-2-ethanesulfonic acid (HEPES); piperazine-N,N'-bis(2-ethanesulfonic acid) (PIPES); N-(2-acetamido)-2-aminoethanesulfonic acid (ACES); N-[tris(hydroxymethyl)methyl]glycine (Tricine); and 2-(N-morpholino)ethanesulfonic acid (MES).

14. A method of stimulating the immune system of a mammal in need thereof by inducing the production of hypercellular bone marrow and extramedullary hematopoiesis, said method comprising administering to said mammal a composition comprising an effective amount of a zwitterion compound or a pharmaceutically acceptable salt thereof, which zwitterion compound is an aliphatic or heterocyclic compound having at least one carbon-nitrogen bond and having an acid group selected from the group consisting of: $SO_3$; $PO_3$; and COO; and an alkaline group selected from the group consisting of: OH; $N^+$; $N^+H$; and $NH_2$ to induce hypercellular bone marrow production and extramedullary hematopoiesis in the mammal.

15. The method of claim 14 wherein the zwitterion compound has a six member heterocyclic ring with a nitrogen atom as a part of the ring.

16. The method of claim 14 which comprises administering from about 0.1 mg/kg to about 5000 mg/kg of the zwitterion compound per body weight of the mammal.

17. The method of claim 14 wherein the zwitterion composition comprises an amino acid and human serum.

18. The method of claim 14, which method of stimulating comprises inducing the production of giant platelets and histocytes.

19. The method of claim 14 wherein the zwitterion compound has a 5 or 6 membered heterocyclic ring with two nitrogen atoms or a nitrogen and an oxygen atom in the ring.

20. The method of claim 14 wherein the zwitterion compound has one or more —$CH_2OH$ groups and a —$CH_2$ COO acid group connected to an intermediate nitrogen atom.

21. The method of claim 14 wherein the zwitterion compound has a pH at 20° C. of 6.15 to 8.4.

22. The method of claim 14 which comprises administering orally over a selected time period from about 0.1 mg/kg to 500 mg/kg of the zwitterion compound per body weight of the patient.

23. The method of claim 14 wherein the zwitterion compound is selected from the group consisting of N-(2-hydroxyethyl)piperazine-N'-2-ethanesulfonic acid (HEPES); piperazine-N,N'-bis(2-ethanesulfonic acid) (PIPES); N-(2-acetamido)-2-aminoethanesulfonic acid (ACES); N-[tris(hydroxymethyl)methyl]glycine (Tricine); and 2-(N-morpholino)ethanesulfonic acid (MES).

* * * * *